United States Patent
Zhao et al.

(10) Patent No.: US 12,156,876 B2
(45) Date of Patent: Dec. 3, 2024

(54) FORMULATIONS OF INFLUENZA THERAPEUTICS

(71) Applicant: COCRYSTAL PHARMA, INC., Bothell, WA (US)

(72) Inventors: Tianjing Zhao, Shanghai (CN); Liang Mao, Shanghai (CN); Irina C. Jacobson, Sammamish, WA (US); Sam S K Lee, Edmonds, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 800 days.

(21) Appl. No.: 17/292,863

(22) PCT Filed: Nov. 13, 2019

(86) PCT No.: PCT/US2019/061065
§ 371 (c)(1),
(2) Date: May 11, 2021

(87) PCT Pub. No.: WO2020/102270
PCT Pub. Date: May 22, 2020

(65) Prior Publication Data
US 2021/0393629 A1     Dec. 23, 2021

Related U.S. Application Data

(60) Provisional application No. 62/760,121, filed on Nov. 13, 2018.

(51) Int. Cl.
*A61K 31/506* (2006.01)
*A61K 9/00* (2006.01)
*A61K 9/16* (2006.01)

(52) U.S. Cl.
CPC ......... *A61K 31/506* (2013.01); *A61K 9/0075* (2013.01); *A61K 9/1623* (2013.01); *A61K 9/1694* (2013.01)

(58) Field of Classification Search
CPC ... A61K 31/506; A61K 9/0075; A61K 9/1623
(Continued)

(56) References Cited

U.S. PATENT DOCUMENTS

| 4,353,656 A | 10/1982 | Sohl et al. |
| 4,778,054 A | 10/1988 | Newell et al. |

(Continued)

FOREIGN PATENT DOCUMENTS

| CA | 3008607 A1 * | 6/2017 | ............ A61K 31/53 |
| CN | 1728988 A | 2/2006 | |

(Continued)

OTHER PUBLICATIONS

Xiong J, Wang J, Hu G, Zhao W, Li J. Design, synthesis and biological evaluation of novel, orally bioavailable pyrimidine-fused heterocycles as influenza PB2 inhibitors. European Journal of Medicinal Chemistry. Jan. 15, 2019;162:249-65. (Year: 2018).*

(Continued)

*Primary Examiner* — Jeffrey S Lundgren
*Assistant Examiner* — Heather Dahlin
(74) *Attorney, Agent, or Firm* — MARSHALL, GERSTEIN & BORUN LLP

(57) ABSTRACT

Provided herein are compositions of an antiviral therapeutic to treat influenza suitable for administration via inhalation.

19 Claims, 3 Drawing Sheets

(58) Field of Classification Search
USPC .................................................. 514/256
See application file for complete search history.

(56) References Cited

U.S. PATENT DOCUMENTS

| | | | |
|---|---|---|---|
| 4,811,731 | A | 3/1989 | Newell et al. |
| 5,035,237 | A | 7/1991 | Newell et al. |
| 5,590,645 | A | 1/1997 | Davies et al. |
| 5,860,419 | A | 1/1999 | Davies et al. |
| 5,873,360 | A | 2/1999 | Davies et al. |
| 6,632,666 | B2 | 10/2003 | Baust et al. |
| 9,339,487 | B2 * | 5/2016 | Miyajima et al. ... A61K 31/151 31/151 |
| 11,014,941 | B2 * | 5/2021 | Jacobson et al. .... C07D 519/00 |

FOREIGN PATENT DOCUMENTS

| | | |
|---|---|---|
| CN | 105848683 A | 8/2016 |
| CN | 105849100 A | 8/2016 |
| EP | 69715 A1 | 1/1983 |
| GB | 2064336 A | 6/1981 |
| GB | 2129691 A | 5/1984 |
| GB | 2169265 A | 7/1986 |
| GB | 2178965 A | 2/1987 |
| GB | 2242134 A | 9/1991 |
| WO | WO-2015073476 A1 | 5/2015 |
| WO | WO-2015073491 A1 | 5/2015 |
| WO | WO-2018/200425 A1 | 11/2018 |

OTHER PUBLICATIONS

Caira MR. Crystalline polymorphism of organic compounds. Design of Organic Solids. 1998:163-208. (Year: 1998).*
SciFinder, CAS Registry No. 2415662-16-5, retrieved Feb. 13, 2024 (Year: 2024).*
Caira, Crystalline Polymorphism of Organic Compounds, Topics in Current Chemistry, vol. 198, pp. 163-208 (Jan. 1998).
International Application No. PCT/US2019/061065, International Search Report and Written Opinion, mailed Feb. 13, 2020.
Xiong et al., Design, synthesis and biological evaluation of novel, orally bioavailable pyrimidine-fused heterocycles as influenza PB2 inhibitors, Eur. J. Med. Chem., 162:249-65 (Jan. 2019).
Kojima, Effective Solid Form Selection for the Pharmaceutical Development, Journal of Pharm. Sci. Technol., 68(5):344-9 (2008).
Japanese Patent Application No. 2021-526323, Office Action, dated Sep. 21, 2023.

* cited by examiner

FORMULATIONS OF INFLUENZA THERAPEUTICS

BACKGROUND

Influenza spreads around the world in seasonal epidemics, resulting in the deaths of hundreds of thousands of people annually-millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogotovirus.

The Influenza virus A genus is responsible for seasonal flu and pandemic flu epidemics. It has one species, influenza A virus, and wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which a potential pandemic threat, H1N2 (endemic in humans and pigs), H9N2, H7N2, H7N3 and H10N7.

The Influenza virus B genus is responsible for seasonal flu, and has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza viruses are very similar in structure across serotypes and genera. The influenza virus genome consists of eight single-stranded RNAs packed into rod-like structures of varying size, known as the ribonucleoprotein complex (RNP). Each RNP contains a unique viral RNA, multiple copies of the scaffolding nucleoprotein, and a heterotrimeric viral polymerase consisting of the PA, PB1, and PB2 subunits, which catalyzes the transcription and replication of the viral genome. Recent biochemical and structural studies of influenza polymerase complex provide insight into the mechanistic understanding of cap-snatching and RNA synthesis by influenza polymerase. Briefly, the PB2 cap-binding domain first sequesters the host pre-mRNAs by binding to their 5' cap. PA, the endonuclease subunit, then cleaves the captured pre-mRNA 10-13 nucleotides downstream of the cap. The PB2 subunit subsequently rotates about 70° to direct the capped primer into the PB1 polymerase active site. The PB1 subunit directly interacts with both PB2 and PA subunits. These subunits contain highly conserved domains among different influenza strains, and have attracted attention as a potential anti-influenza drug target. In addition to the polymerase complex, the influenza genome encodes its own neuraminidase (NA), hemagglutinin (HA), nucleoprotein (NP), matrix proteins, M1 and M2, and non-structural proteins, NS1 and NS2. NA is the target for the antiviral drugs oseltamivir (Tamiflu®) and zanamivir (Relenza®). These drugs are sialic acid analogues which inhibit the enzymatic activity of NA, thus slowing down the release of progeny virus from infected cells.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with NA inhibitors being particularly effective, but viruses can develop resistance to the approved NA antiviral drugs. Also, emergence of a multidrug-resistant pandemic influenza A viruses has been well documented. Drug-resistant pandemic influenza A becomes a substantial public health threat. In addition to the drug resistant influenza A viruses, the NA inhibitors are approved for the treatment early influenza infection (within 48 hours of influenza symptom onset).

Thus, there is a need for formulations of antiviral agents against influenza virus that can be administered via pulmonary delivery.

SUMMARY

Provided herein are formulations of Compound 1 and a filler. In some cases, the formulation comprises (a) Compound 1 or a pharmaceutically acceptable salt thereof; and (b) a filler. In various cases, the formulation consists essentially of (a) Compound 1 or a pharmaceutically acceptable salt thereof; and (b) a filler. In various cases, the formulation is a powder formulation for inhalation administration comprising (a) Compound 1 or a pharmaceutically acceptable salt thereof; and (b) a filler consisting essentially of lactose monohydrate, wherein the formulation has a particle size distribution characterized by a volume mean diameter (VMD) of 1 to 2 μm, with a $D_{10}$ of 0.5 μm to 0.7 μm, a $D_{50}$ of 1 μm to 1.4 μm, and a $D_{90}$ of 2.5 μm to 2.8 μm. In some cases, the VMD is 1.5 μm, with a $D_{10}$ of 0.6 μm, a $D_{50}$ of 1.3 μm, and a $D_{90}$ of 2.8 μm.

In various embodiments, the filler comprises lactose, or more specifically, comprises lactose monohydrate. In some cases, the filler is micronized. The filler can have a volume mean diameter (VMD) of 0.5 μm to 10 μm. In some cases, the filler has a VMD of 1.5 to 5 μm.

In various embodiments, Compound 1 or salt thereof is micronized. Compound 1 can be crystallized (in crystal form), and in some cases, is present as a micronized crystal. In some cases, the crystal form of Compound 1 is Form B and has an x-ray powder diffraction (XRPD) pattern exhibiting 2θ values of 5.6, 6.8, 8.4, 10.1, 10.6, 11.3, 15.1, 15.8, 18.0, 18.5, 19.1, 20.4, and 20.9, ±0.2°. In various cases, Compound 1 (e.g., as Form B) has a melting point of 280° C. to 283° C. In various cases, Compound 1 can be as Form A or Form C.

Compound 1 or salt thereof can have a volume mean diameter (VMD) of 0.5 μm to 10 μm. In some cases, Compound 1 VMD is 1.5 to 5 μm. The formulations disclosed herein can have a weight ratio of Compound 1 or salt thereof to filler of 1:3 to 1:5. In some cases, the weight ratio is 1:4.

The formulations disclosed herein can be adaptable as an inhalation formulation. They are contemplated as formulations to deliver Compound 1 or salt thereof to a subject via inhalation. The formulations disclosed herein can, upon administration via inhalation, provide a drug concentration in lung that is at least 50 times that of drug concentration in plasma 1 hour after inhalation. In various cases, the drug concentration in lung is at least 100 times that of drug concentration in plasma 1 hour after inhalation. In various cases, the drug concentration in lung is at least 50 times that of drug concentration in plasma 24 hours after inhalation. In various cases, the drug concentration in lung is at least 100 times that of drug concentration in plasma 24 hour after inhalation. In various cases, the drug concentration in lung is at least 50 times that of drug concentration in plasma 48 hours after inhalation. In various cases, the drug concentration in lung is at least 100 times that of drug concentration in plasma 48 hour after inhalation.

Further provided herein are methods of treating or preventing influenza virus infection or replication in a subject in need thereof comprising administering to the subject a formulation as disclosed herein.

Also provided are methods of making a formulation as disclosed herein by (a) micronizing Compound 1 or salt thereof to form particles of Compound 1; (b) optionally micronizing the filler to form particles of the filler; and (c) blending the micronized Compound 1 or salt thereof and the optionally micronized filler to form the formulation. In various cases, the micronizing of the Compound 1 or salt thereof or of the filler is performed via manual grinding or jet milling.

In various cases, the method can further comprise crystallizing Compound 1 or salt thereof prior to micronizing. In some cases, the crystallizing comprises admixing Compound 1 or salt thereof and ethanol at a temperature of at least 50° C., cooling to room temperature to allow for crystallization of Compound 1 or salt thereof, and collecting the crystals via filtration, and optionally drying the crystals prior to micronizing. The temperature of the admixing can be 75° C. In some cases, the admixing occurs for 4 to 10 hours.

Further provided herein are crystalline forms of Compound 1. In some cases, Compound 1 is as Form B, and the crystal can exhibit an x-ray powder diffraction (XRPD) pattern having 2θ values of 5.6, 6.8, 8.4, 10.1, 10.6, 11.3, 15.1, 15.8, 18.0, 18.5, 19.1, 20.4, and 20.9, ±0.2°. In some cases, Form B has an XRPD as substantially shown in FIG. 1. In various cases, Form B has a melting point of 280° C. to 283° C. In some cases, Compound 1 is as Form C, and the crystal can exhibit an XRPD pattern substantially as shown in FIG. 3 (middle spectrum).

DETAILED DESCRIPTION

Figure 1:
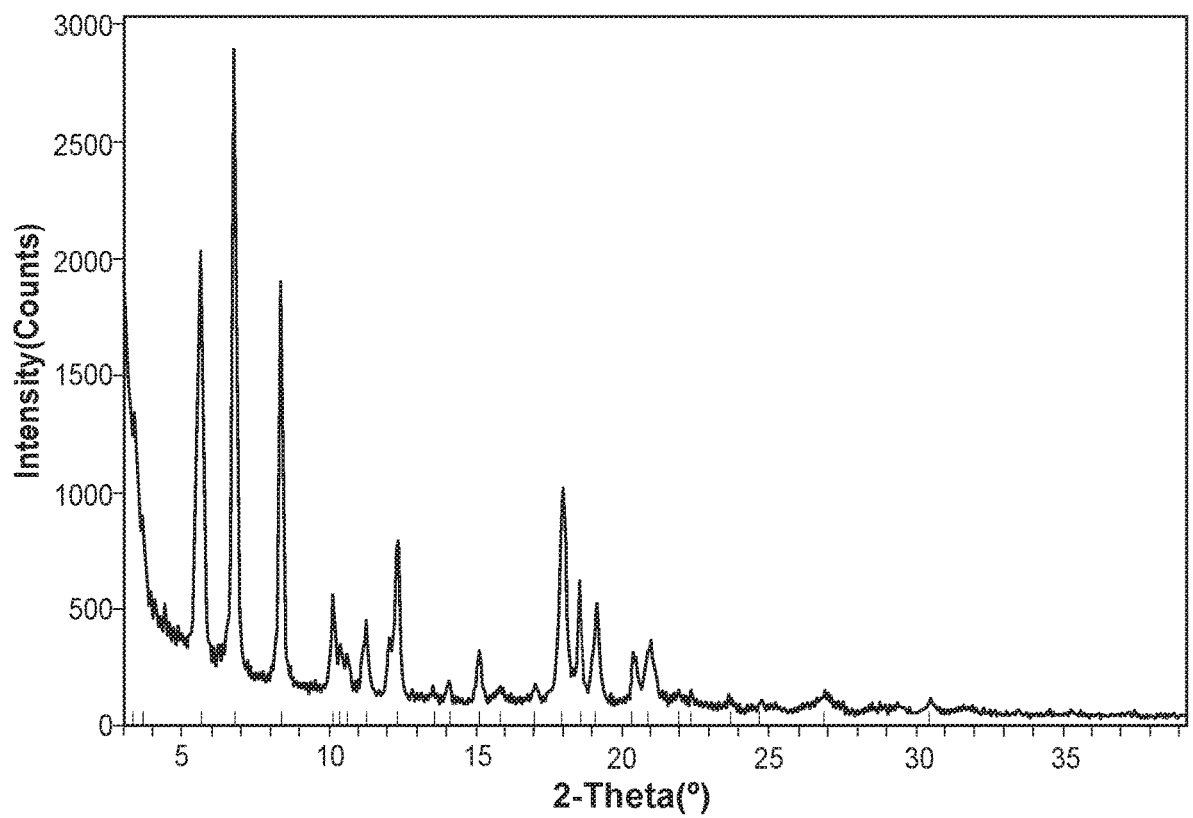
FIG. 1 shows an XRPD (X-ray powder diffraction) pattern of crystalline Compound 1 as Form B.

Disclosed herein are compositions of an anti-influenza compound and uses of these compositions in inhibiting influenza virus activity. In some aspects, the present disclosure is generally related to the use of the compositions described herein for inhibiting the replication of influenza viruses in a biological sample or in a patient, for reducing the amount of influenza viruses (reducing viral titer) in a biological sample or in a patient, and for treating or preventing influenza in a patient. The compositions disclosed herein can be for pulmonary administration to the subject, patient, or host, e.g., via inhalation.

The compositions disclosed herein are useful as therapy against an influenza virus infection. Thus, in some aspects, there is provided use of a therapeutically effective amount of a composition as disclosed herein for the treatment or prevention of influenza virus infection or replication in a human patient. For example, the influenza virus can be a pandemic or drug-resistant pandemic/seasonal influenza virus.

In various cases, there is provided a method of inhibiting endonuclease activity of influenza polymerase in an influenza A or B virus, comprising contacting the virus with a composition as disclosed herein. In some cases, there is provided a method for treating or preventing an Influenza A or Influenza B infection in a host, comprising administering to the host a therapeutic amount of a composition as disclosed herein. In various cases, there is provided a method for reducing endonuclease activity of influenza polymerase in an influenza A or B virus in a host, comprising administering to the host a therapeutic amount of a composition as disclosed herein. In some cases, there is provided a method for reducing influenza virus replication in a host, comprising administering to the host a therapeutic amount of a composition as disclosed herein.

Compound 1

The compositions disclosed herein comprise, among other things, 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid, alternatively referred to herein as "Compound 1". The active moiety of Compound 1 is believed to be a CAP-binding PB2 domain inhibitor.

Compound 1 can exist in free form, or, where appropriate, as a salt. Those salts that are pharmaceutically acceptable are of particular interest since they are useful in administering the compounds that are components of the described combinations for medical purposes. Salts that are not pharmaceutically acceptable are useful in manufacturing processes, for isolation and purification purposes, and in some instances, for use in separating stereoisomeric forms of the compounds described herein or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxylic acid group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

The components of the combinations can be present in the form of a solvate. The term "solvate" refers to a molecular complex of a compound (including a salt thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound and water.

Compound 1, or salt or solvate thereof, can be micronized for use in the compositions disclosed herein. Micronized refers to a solid form having particles of less than 15 μm. In various cases, Compound 1, or salt or solvate thereof, can be present as particles of 0.5 μm to 10 μm, e.g., 1 μm to 10 μm, 2 μm to 10 μm, 3 μm to 10 μm, 4 μm to 10 μm, 5 μm to 10 μm, 6 μm to 10 μm, 1 μm to 7 μm, 2 μm to 7 μm, 3 μm to 7 μm, 2 μm to 6 μm, 2 μm to 5 μm, 3 μm to 7 μm, or 3 μm to 6 μm.

Compound 1, or salt or solvate thereof, can be micronized using any known technique. In some cases, the micronization is via jet milling or manual grinding.

Compound 1 can be present in the disclosed compositions as a crystalline form.

Form B: In various cases, the crystalline form can be characterized by an X-ray powder diffraction pattern, obtained as set forth in the Examples, having peaks at about 5.6, 6.8, 8.4, 10.1, 10.6, 11.3, 15.1, 15.8, 18.0, 18.5, 19.1, 20.4, and 20.9, ±0.2° 2θ using Cu Kα radiation, termed "Form B". In some embodiments, crystalline Compound 1 can be characterized by an X-ray powder diffraction pattern substantially as depicted in FIG. 1 wherein by "substantially" is meant that the reported peaks can vary by about ±0.2°. It is well known in the field of XRPD that, while relative peak heights in spectra are dependent on a number of factors, such as sample preparation and instrument geometry, peak positions are relatively insensitive to experimental details.

Figure 2:
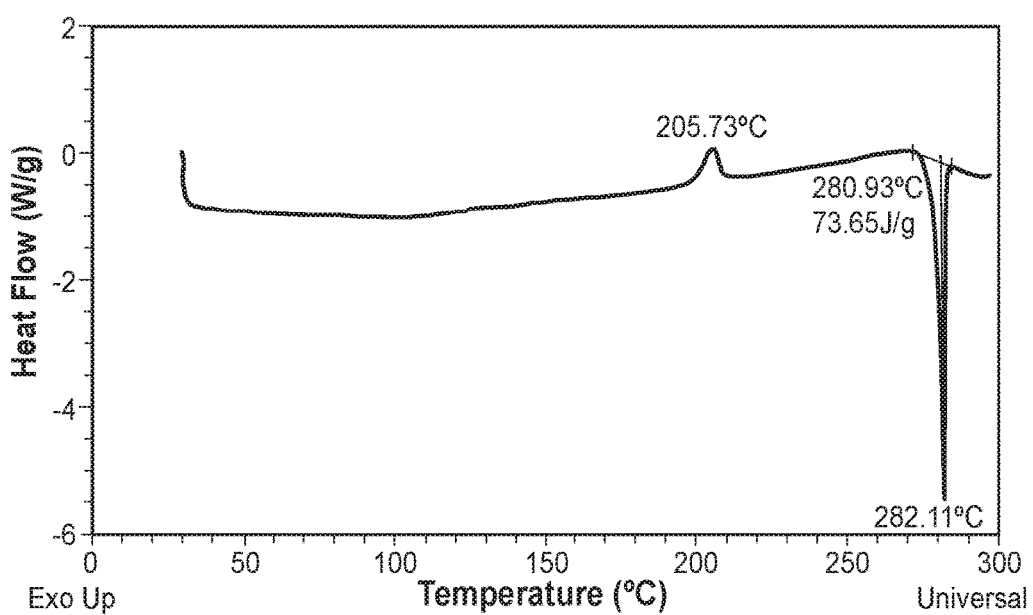
FIG. 2 shows a DSC (differential scanning calorimetry) thermogram of crystalline Compound 1 as Form B.

In some cases, crystalline Compound 1 can be characterized by a differential scanning calorimetry (DSC) thermogram, e.g., as substantially shown in FIG. 2. In some cases, the crystalline Compound 1 has a melting temperature of 280° C. to 283° C., or about 282° C.

Figure 4:
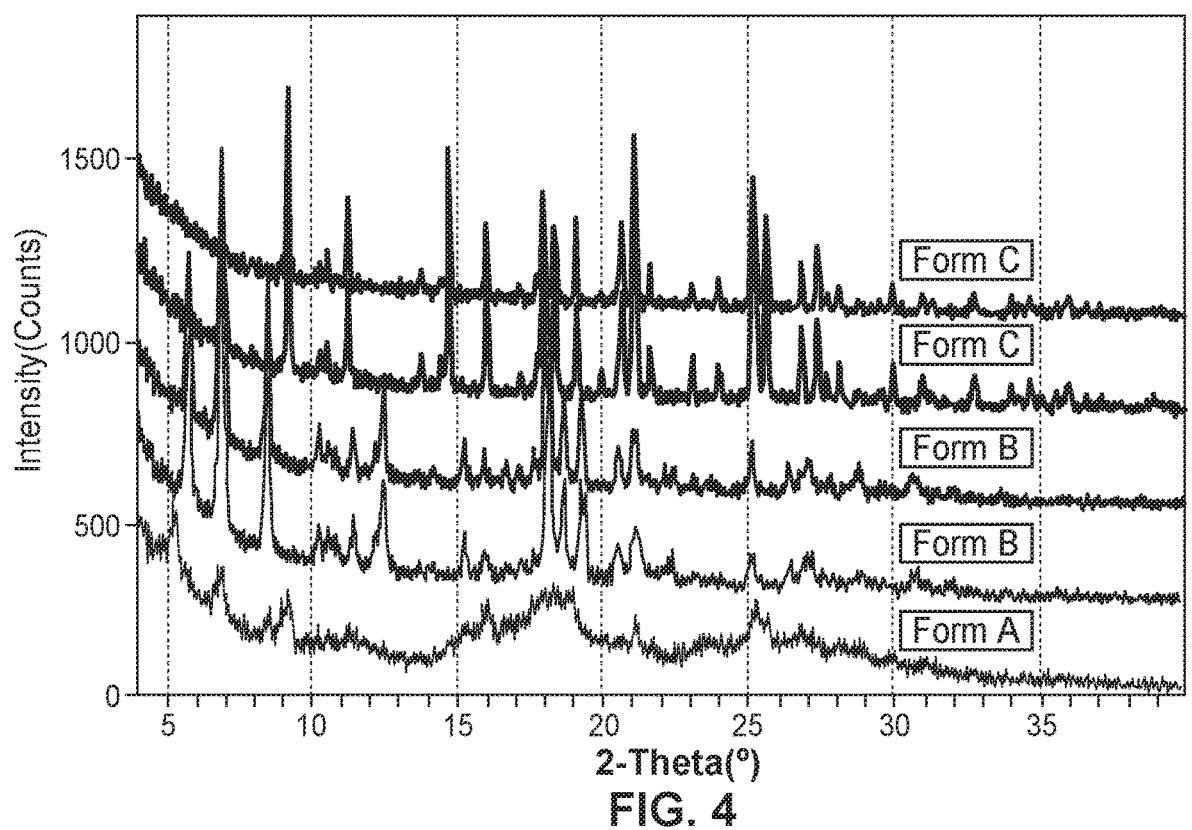
FIG. 4 shows a comparison of XRPD patterns of crystalline Compound 1, as formed via slurry method, for (from top to bottom) Form C, Form C, Form B, Form B, and Form A.

Form A: In various cases, the crystalline form can be characterized by an X-ray powder diffraction pattern, obtained as set forth in the Examples, having 2θ peaks substantially as shown in FIG. 4, termed "Form A". By "substantially" is meant that the reported peaks can vary by about ±0.2°. It is well known in the field of XRPD that, while relative peak heights in spectra are dependent on a number of factors, such as sample preparation and instrument geometry, peak positions are relatively insensitive to experimental details.

Figure 3:
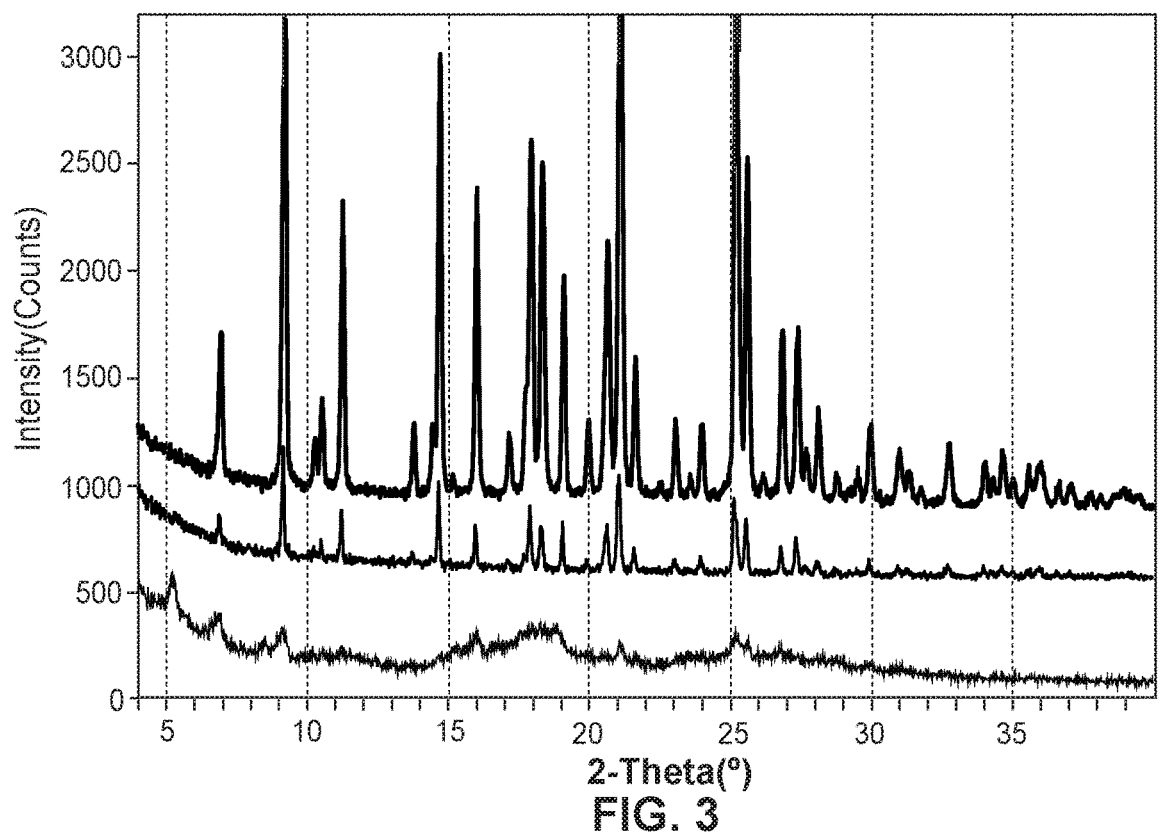
FIG. 3 shows a XRPD pattern of crystalline Compound 1 as Form C (middle spectrum).

Form C: In various cases, the crystalline form can be characterized by an X-ray powder diffraction pattern, obtained as set forth in the Examples, having 2θ peaks substantially as shown in FIG. 3 (middle spectrum), termed "Form C". By "substantially" is meant that the reported peaks can vary by about ±0.2°. It is well known in the field of XRPD that, while relative peak heights in spectra are dependent on a number of factors, such as sample preparation and instrument geometry, peak positions are relatively insensitive to experimental details.

Compound 1 can also be present as Form D or Form E, as discussed in the Examples section below.

Filler

The compositions disclosed herein comprise a filler. Fillers can include microcrystalline cellulose, dicalcium phosphate, lactose (including lactose monohydrate), trehalose, sucrose, mannose, mannitol, sorbitol, calcium carbonate, starches, and magnesium or zinc stearates. In some cases, the filler is one or more of lactose, glucose, and sodium starch glycolate. In some cases, the filler comprises lactose, e.g., lactose monohydrate. In some cases, the filler is crystalline lactose monohydrate, such as Inhalac®, e.g., Inhalac® 400.

The filler can be micronized for use in the compositions disclosed herein. Micronized refers to a solid form having particles of less than 15 μm. In various cases, the filler can be present as particles of 0.5 μm to 10 μm, e.g., 1 μm to 10 μm, 2 μm to 10 μm, 3 μm to 10 μm, 4 μm to 10 μm, 5 μm to 10 μm, 6 μm to 10 μm, 1 μm to 7 μm, 2 μm to 7 μm, 3 μm to 7 μm, 2 μm to 6 μm, 2 μm to 5 μm, 3 μm to 7 μm, or 3 μm to 6 μm.

The filler can be micronized using any known technique. In some cases, the micronization is via jet milling or manual grinding.

In various cases, the compositions disclosed herein comprise Compound 1 and the filler in a weight ratio of 1:3 to 1:5. In various cases, the weight ratio is about 1:4.

Pulmonary Administration and Devices

In some embodiments, the compositions described herein are adapted to be administered to the lower respiratory tract (e.g., the lungs) directly through the airways by inhalation. The compositions for administration by inhalation can be an inhalable powder, and can be administered using powder inhaler devices. Such devices are well known.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360, and 5,590,645 (all illustrating the "Diskus" device), or GB2178965, GB2129691, GB2169265, U.S. Pat. Nos. 4,778,054, 4,811,731 and 5,035,237 (which illustrate the "Diskhaler" device), or EP 69715 ("Turbuhaler" device), or GB 2064336 and U.S. Pat. No. 4,353,656 ("Rotahaler" device). Multiple doses may be stored in a reservoir or in multiple, individually packaged doses stored in, for example, blisters or capsules. Examples of suitable devices include, but are not limited to, the TURBUHALER (Astra Zeneca), CLICKHALER (Innovata Biomed), EASYHALER (Orion), ACCUHALER, DISKUS, DISKHALER, ROTAHALER (GlaxoSmithKline), HANDIHALER, INHALATOR, AEROHALER (Boehringer Ingelheim), AEROLIZER (Schering Plough), and NOVOLIZER (ASTA Medica).

Upon administration, e.g., via inhalation, the compositions disclosed herein show high levels of drug exposure in the lungs, compared to exposure in plasma. These high drug exposure levels are beneficial for several reasons. First, pulmonary administration provides rapid delivery of the therapeutic to the point of infection. Second, maintaining the therapeutic in the lungs while minimizing plasma exposure allows for reduced systemic adverse events, since minimal therapeutic travels away from the point of infection. Third, concentrating the exposure at the lungs allows for maximizing therapeutic benefit at the point of infection (e.g., the lungs).

In some cases, administration via inhalation of a composition as disclosed herein provides exposure in lungs to Compound 1 that is 50 times greater than exposure in plasma after 1 hour. In various cases, exposure after 1 hour is 60 times greater in lungs over plasma, or 70 times greater, or 80 times greater, or 90 times greater, or 100 times greater, or 125 times greater, or 150 times greater.

In some cases, administration via inhalation of a composition as disclosed herein provides exposure in lungs to Compound 1 that is 50 times greater than exposure in plasma after 24 hours. In various cases, exposure after 24 hours is 60 times greater in lungs over plasma, or 70 times greater, or 80 times greater, or 90 times greater, or 100 times greater, or 125 times greater, or 150 times greater.

In some cases, administration via inhalation of a composition as disclosed herein provides exposure in lungs to Compound 1 that is 50 times greater than exposure in plasma after 48 hours. In various cases, exposure after 48 hours is 60 times greater in lungs over plasma, or 70 times greater, or 80 times greater, or 90 times greater, or 100 times greater, or 125 times greater, or 150 times greater.

In various cases, even after 4 days post-administration via inhalation, the exposure of Compound 1 in lung is at least 100 times greater than that in plasma.

Methods of Use

The compositions described herein can be used to reduce viral titer in a biological sample (e.g., an infected cell culture) or in humans (e.g., lung viral titer in a patient).

The terms "influenza virus mediated condition," "influenza infection," or "Influenza," as used herein, are used interchangeably to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenza virus A, Influenza virus B, Influenza virus C, Isavirus and Thogotovirus. Influenza virus A genus has one species, influenza A virus which can be subdivided into different serotypes based on the antibody response to these viruses: H1N1, H2N2, H3N2, H5N1, H7N7, H1N2, H9N2, H7N2, H7N3 H7N9, and H10N7. Influenza virus B genus has one species, influenza B virus. Influenza B almost exclusively infects humans and is less common than influenza A. Influenza virus C genus has one species, influenza virus C virus, which infects humans and pigs and can cause severe illness and local epidemics. However, influenza virus C is less common than the other types and usually seems to cause mild disease in children.

In some embodiments, influenza or influenza viruses are associated with influenza virus A or B. In some embodiments, influenza or influenza viruses are associated with Influenza virus A. In some specific embodiments, influenza virus A is H1N1, H2N2, H3N2, H7N9, or H5N1. In some embodiments, the disclosed combinations are effective to inhibit growth or replication of a pandemic or drug-resistant pandemic/seasonal influenza virus.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness"). Usually, laboratory data is needed to confirm the diagnosis.

The terms "disease," "disorder," and "condition" may be used interchangeably herein to refer to an influenza virus mediated medical or pathological condition.

As used herein, the terms "subject," "host," and "patient" are used interchangeably. The terms "subject", "host", and "patient" may refer to an animal (e.g., a bird such as a chicken, quail or turkey, or a mammal), specifically a mammal, such as a non-primate (e.g., a cow, pig, horse, sheep, rabbit, guinea pig, rat, cat, dog, or mouse) or a primate (e.g., a monkey, chimpanzee, or human), and more specifically a human. In some embodiments, the subject is a non-human animal such as a farm animal (e.g., a horse, cow, pig or sheep), or a pet (e.g., a dog, cat, guinea pig or rabbit). In a preferred embodiment, the subject is a human.

The term "biological sample," as used herein, includes, without limitation, cell cultures or extracts thereof; biopsied material obtained from a mammal or extracts thereof; blood, saliva, urine, feces, semen, tears, or other body fluids or extracts thereof.

As used herein the term "inhibition of the replication of influenza viruses" includes both the reduction in the amount of virus replication (e.g., a reduction by at least 10%) up to and including the complete arrest of virus replication (i.e., 100% reduction in the amount of virus replication). In some embodiments, the replication of influenza viruses is inhibited by at least 50%, at least 65%, at least 75%, at least 85%, at least 90%, or at least 95%.

Influenza virus replication can be measured by any suitable method known in the art. For example, influenza viral titer in a biological sample (e.g., an infected cell culture) or in humans (e.g., lung viral titer in a patient) can be measured. More specifically, for cell-based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed, and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer" or "titer" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}, 10^{-2}, 10^{-3}, \ldots, 10^{-8}$. The lowest concentration of virus that still infects cells is the viral titer.

As used herein, the terms "treat", "treatment," and "treating" refer to both therapeutic and prophylactic treatments. For example, therapeutic treatments include the reduction or amelioration of the progression, severity and/or duration of influenza virus-mediated conditions, or the amelioration of one or more symptoms (specifically, one or more discernible symptoms) of influenza virus-mediated conditions, resulting from the administration of one or more therapies (e.g., one or more therapeutic agents such as a compound or composition described herein). In specific embodiments, the therapeutic treatment includes the amelioration of at least one measurable physical parameter of an influenza virus-mediated condition. In other embodiments, the therapeutic treatment includes the inhibition of the progression of an influenza virus-mediated condition, either physically by, e.g., stabilization of a discernible symptom, physiologically by, e.g., stabilization of a physical parameter, or both. In other embodiments, the therapeutic treatment includes the reduction or stabilization of influenza viruses mediated infections. Antiviral drugs can be used in the community setting to treat people who already have influenza to reduce the severity of symptoms and reduce the number of days that they are sick.

The terms "prophylaxis," "prophylactic", "prophylactic use," and "prophylactic treatment," as used herein, refer to any medical or public health procedure whose purpose is to prevent, rather than treat or cure a disease. As used herein, the terms "prevent," "prevention," and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g., small molecule drugs, rather than vaccines for the prevention of a disorder or disease.

Prophylactic use includes use in situations in which an outbreak has been detected to prevent contagion or spread of the infection in places where many people that are at high risk of serious influenza complications live in close contact with each other (e.g., in a hospital ward, daycare center, prison, nursing home, etc.). It also includes the use among populations who require protection from influenza but who do not get protection after vaccination (e.g., due to weak immune system), to whom the vaccine is unavailable, or who cannot receive the vaccine because of side effects. It also includes use during the two weeks following vaccination, or during any period after vaccination but before the vaccine is effective. Prophylactic use may also include treating a person who is not ill with the influenza or not considered at high risk for complications, to reduce the chances of getting infected with the influenza and passing it on to a high-risk person in close contact with him or her (e.g., healthcare workers, nursing home workers, etc.).

As used herein, and consistent with the usage of the United States Centers for Disease Control and Prevention (US CDC), an influenza "outbreak" is defined as a sudden increase of acute febrile respiratory illness (AFRI) occurring within a 48- to 72-hour period, in a group of people who are near each other (e.g., in the same area of an assisted living facility, in the same household, etc.) over the normal background rate or when any subject in the population being analyzed tests positive for influenza.

In some embodiments, the compositions are useful as a preventative or prophylactic measure to a patient, specifically a human, having a predisposition to complications resulting from infection by an influenza virus. The compositions can be useful in prophylactic methods in situations in which an index case or an outbreak has been confirmed, to prevent the spread of infection in the rest of the community or population group.

As used herein, an "effective amount" refers to an amount sufficient to elicit the desired biological response. In the present disclosure, the desired biological response is to inhibit the replication of influenza virus, to reduce the amount of influenza virus, or to reduce or ameliorate the severity, duration, progression, or onset of an influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. For example, 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof can be administered to a subject in a dosage range from between approximately 0.01 to 100 mg/kg body weight/day for therapeutic or prophylactic treatment.

As used herein, a "safe and effective amount" of a compound or composition described herein is an effective amount of the compound or composition which does not cause excessive or deleterious side effects in a patient.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe a safe and effective amount of the compounds described herein required to treat, to prevent, inhibit (fully or partially) or arrest the progress of the disease.

Dosages of Compound 1 can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, Compound 1 can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, Compound 1 can be administered to a patient within, for example, 2 days of onset of symptoms in the index case, and can be continued for any suitable duration, for example, for 7 days, 10 days, 14 days, 20 days, 28 days, 35 days, 42 days, etc.

EXAMPLES

Polymorph Screening for Compound 1 (Slurry Method):

About 10 mg of Compound 1 was added in 200 µL various solvents—methyl t-butyl ether (MTBE), methanol (MeOH), ethanol (EtOH), isopropyl alcohol (IPA), isopropyl alcohol and ethyl acetate in 5/5 volume ratio (IPA/EtOAc), ethyl acetate (EtOAc), isopropyl alcohol and water in 8/2 volume ratio, acetonitrile (ACN), acetone, and tetrahydrofuran (THF). Each suspension was stirred at 700 rpm for 24 hrs at 40° C. The residues of the compound were separated by centrifuge (10 min at 14,000 rpm) and further dried for overnight in the vacuum oven at 30° C. If a clear solution remained, the solution was dried under vacuum to generate dry solid. The dry solid was analyzed by XRPD, and assigned a Form. The results are shown in the Table below.

| Solvent | Characterizaiton from XRPD |
| --- | --- |
| MTBE | Pale yellow solid, Form A |
| MeOH | Pale yellow solid, Form B |
| EtOH | Pale yellow solid, Form B |
| IPA | Pale yellow solid, Form B |
| IPA/EtOAc (5/5, v/v) | Pale yellow solid, Form B |
| EtOAc | Pale yellow solid, Form B |
| IPA/H$_2$O (8/2, v/v) | Pale yellow solid, Form C |
| ACN | Pale yellow solid, Form C |
| Acetone | Pale yellow solid, Form D |
| THF | Pale yellow solid, Amorphous |

XRPD patterns of the crystals was obtained using a Bruker D8 Advance instrument with the following parameters. Results of an XRPD analysis for Form B are shown in FIG. 1. Results for Form C are shown in FIG. 3. Results for Forms A, B, and C are shown in FIG. 4.

| Parameters | Settings/Values |
| --- | --- |
| Time per step | 0.12 s |
| X-Ray tube setting | Voltage: 40 kV; Current: 40 mA |
| Scan scope | 4 to 40 deg |
| Sample rotation speed | 15 rpm |
| Scanning rate | 10 deg./min |
| Parameter | 2 theta |

A DSC of the crystals of Form B was obtained using TA Q2000 instrument with the following parameters, and results of the DSC are shown in FIG. 2.

| Parameters | DSC |
| --- | --- |
| Method | Ramp |
| Temperature range | 30° C.-300° C. |
| Heating rate | 10° C./min |
| Purge gas | N$_2$ |
| Pan type | Aluminum, crimped |

Figure 5:
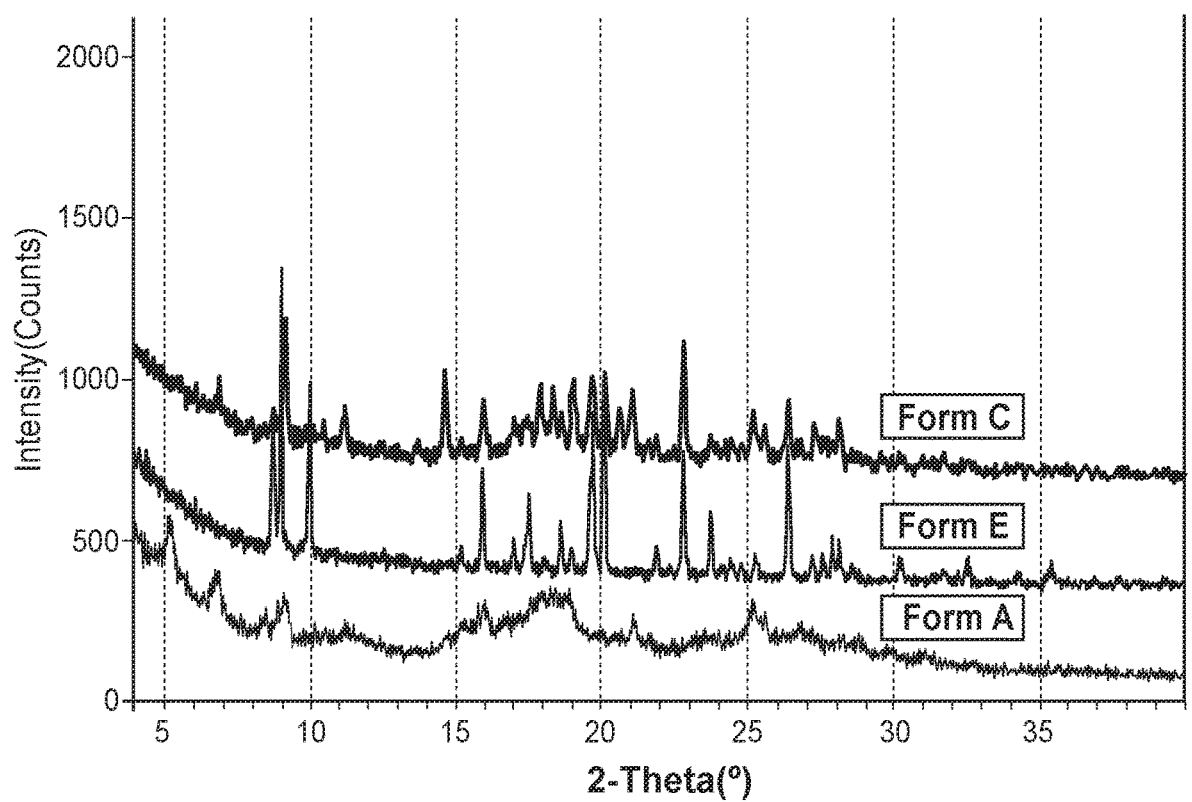
FIG. 5 shows a comparison of XRPD patterns of crystalline Compound 1, as formed via anti-solvent method, for (from top to bottom) Form C, Form E, and Form A.

Polymorph Screening of Compound 1 (Anti-Solvent Method): About 25 mg of Compound 1 was weighed into glass vial, followed to add 0.5 mL dimethyl acetamide (DMA) to achieve concentration of 50 mg/mL as a clear solution. Then, to this solution anti-solvents were added dropwise with stirring at 700 rpm, at room temperature. The resulting crystals were then collected centrifugation. The crystals were analyzed by XRPD, with results shown in FIG. 5, where top is Form E, middle is Form C, and bottom is Form A.

| Anti-solvent | Anti-solvent volume added (mL) | Observation | XRPD |
| --- | --- | --- | --- |
| ACN | 1.5 | Homogeneous opaque suspension | Form E |
| Ethanol | 5 | Clear solution | |
| IPA | 5 | Clear solution | |
| Acetone | 5 | Clear solution | |
| Water | 0.5 | Homogeneous opaque suspension | Form C |

Polymorph Formation at Different Temperatures—Slurry: About 25 mg of Compound 1 was weighed out into glass vial, followed by adding 500 µL of different solvents. The solution was stirred at 700 rpm for 3 days at 55° C. or 25° C. The residues of the compound were separated by centrifuge (10 min at 10,000 rpm) and further dried for 2 days in the vacuum oven at 30° C. The dry solid was analyzed by XRPD. A summary of forms obtained under different conditions are shown below.

| Solvent | Process | XRPD |
| --- | --- | --- |
| Ethanol | Slurry/25° C. | Form B |
| | Slurry/55° C. | Form B |
| ACN | Slurry/25° C. | Form A |
| | Slurry/55° C. | Form A |
| Acetone | Slurry/25° C. | Form A |
| | Slurry/55° C. | Form C |
| MeOH | Slurry/25° C. | Form B |
| | Slurry/55° C. | Form B |
| MTBE | Slurry/25° C. | Form A |
| | Slurry/55° C. | Form A |
| IPA | Slurry/25° C. | Form A |
| | Slurry/55° C. | Form A |
| EtOAc | Slurry/25° C. | Form A |

| Solvent | Process | XRPD |
|---|---|---|
| IPA/H$_2$O (8/2) | Slurry/55° C. | Form C |
| | Slurry/25° C. | Form C |
| | Slurry/55° C. | Form C |
| EtOH/H$_2$O (8/2) | Slurry/25° C. | Form C |
| | Slurry/55° C. | Form C |

Polymorph Formation at Different Temperatures: About 50 mg of Compound 1 was weighed out into glass vial, followed by addition of 500 μL of different solvents. The solution was then stirred at 700 rpm for 3 days at 55° C. The solid was separated by centrifuge (10 min at 10,000 rpm) and further dried for 2 days in the vacuum oven at 30° C. The solid was analyzed by XRPD.

About 25 mg of Compound 1 was weighed out into glass vial, then stored at 25° C./60% RH or 40° C./75% RH for 1 week. Then the samples were analyzed by XRPD.

The XRPD results are summarized below.

| Solvent | Water activity | Process | XRPD |
|---|---|---|---|
| 0% H$_2$O Acetone | 0 | Slurry/55° C. | Amorphous + Form C |
| 3% H$_2$O/Acetone (V/V) | 0.32 | Slurry/55° C. | Form C |
| 11% H$_2$O/Acetone (V/V) | 0.56 | Slurry/55° C. | Form C |
| 16% H$_2$O/Acetone (V/V) | 0.63 | Slurry/55° C. | Form C |
| 31% H$_2$O/Acetone (V/V) | 0.76 | Slurry/55° C. | Form C |
| 42% H$_2$O/Acetone (V/V) | 0.81 | Slurry/55° C. | Form C |
| 79% H$_2$O/Acetone (V/V) | 0.94 | Slurry/55° C. | Form C |
| Expose to 25 C./60% RH | 0.60 | — | Form A |
| Expose to 40 C./75% RH | 0.75 | — | Form A |

Polymorph Formation at Different Temperatures (Anti-Solvent): About 50 mg of Compound 1 was weighed out into glass vial, followed by addition of 1 mL of DMA, which was then sonicated to obtain a clear solution. The solution was then stirred at 700 rpm at 55° C., then adding the anti-solvent either with fast precipitation or slow precipitation. Fast precipitation: add certain amount of anti-solvent at fast speed, and filtrate solid within 1 hour. Slow precipitation: add certain amount of anti-solvent at slow speed, and filtrate solid after slurry for 3 days. The resulting solid was separated by centrifuge (10 min at 10,000 rpm) and further dried for 2 days in the vacuum oven at 30° C. The solid was analyzed by XRPD. The XRPD results are shown below.

| Stock solution | Anti-solvent | Process | Anti-solvent volume added (mL) | Observation | XRPD |
|---|---|---|---|---|---|
| 50 mg API in DMA (50 mg/mL) | ACN | Fast precipitation | 3.0 | Hazy suspension with precipitate | Form A |
| | | Slow precipitation | 3.0 | Homogeneous suspension | Form F |
| | Water | Fast precipitation | 1.0 | Homogeneous suspension | Form A |
| | | Slow precipitation | 1.0 | Homogeneous suspension | Form A |

Summary of Polymorph Study Results

| | Method and Temperature Slurry | | | |
|---|---|---|---|---|
| Solvent | 25° C. | 40° C. | 55° C. | 70° C. |
| MTBE | Form A | Form A | Form A | — |
| MeOH | Form B | Form B | Form B | — |
| EtOH | Form B | Form B | Form B | Form B |
| IPA | Form A | Form B | Form A | — |
| IPA/EtOAc (5/5, v/v) | — | Form B | — | — |
| EtOAc | Form A | Form B | Form C | — |
| IPA/H$_2$O (8/2, v/v) | Form C | Form C | Form C | — |
| EtOH/H$_2$O (8/2, v/v) | Form C | — | Form C | Form C |
| ACN | Form A | Form C | Form A | — |
| Acetone | Form A | Form D | Form C | — |
| THF | — | Amorphous | — | — |
| 0% H$_2$O Acetone | — | — | Amorphous + Form C | — |
| 3% H$_2$O/Acetone (V/V) | — | — | Form C | — |
| 11% H$_2$O/Acetone (V/V) | — | — | Form C | — |
| 16% H$_2$O/Acetone (V/V) | — | — | Form C | — |
| 31% H$_2$O/Acetone (V/V) | — | — | Form C | — |
| 42% H$_2$O/Acetone (V/V) | — | — | Form C | — |
| 79% H$_2$O/Acetone (V/V) | — | — | Form C | — |
| Expose to 25° C./60% RH | — | — | Form A | — |
| Expose to 40° C./75% RH | — | — | Form A | — |

| | | Method and Temperature Anti-solvent | | |
|---|---|---|---|---|
| Solution | Solvent | Normal (25° C.) | Fast (55° C.) | Slow (55° C.) |
| 50 mg Compound 1 in DMA (50 mg/mL) | ACN | Form E | Form A | Form F |
| | water | Form C | Form A | Form A |
| | IPA | — | — | — |
| | EtOH | — | — | — |
| | Acetone | — | — | — |

Micronization of Compound 1: The crystallized Compound 1 (Form B) was added to jet milling gradually with the injector gas pressure 4.5 bar, the grinding gas to be 4 bar. The micronized product exhibited the characteristic peaks that are same with the compound before micronization. In addition, DSC results confirmed that a contiguous exothermic peak at 198.27° C. and a single endothermic peak at 280.40° C. before decomposition, identical to those observed with the sample before micronization. The particle size distribution (PSD) of dry dispersion results showed that the particle size of the micronized compound is VMD=2.08 μm, $D_{10}$=0.65 μm, $D_{50}$=1.44 μm and $D_{90}$=4.21 μm.

Micronization of Lactose Monohydrate: Several lactose monohydrate materials were tested in characterized as summarized in the table below.

| | Process parameters | | | | | |
|---|---|---|---|---|---|---|
| | Injector gas | Grinding gas | PSD(μm) | | | |
| Sample | press/bar | press/bar | VMD | $D_{10}$ | $D_{50}$ | $D_{90}$ |
| Inhalac 70 | N/A | N/A | 211.43 | 128.70 | 212.61 | 294.71 |
| Inhalac 70-Micronized | 4 | 3.5 | 3.77 | 1.09 | 3.43 | 7.03 |
| Inhalac 230 | N/A | N/A | 94.60 | 40.19 | 95.47 | 145.35 |
| Inhalac 230-Micronized | 4 | 3.5 | 4.01 | 1.11 | 3.55 | 7.49 |
| Inhalac 250 | N/A | N/A | 52.25 | 14.95 | 49.74 | 90.85 |
| Inhalac 250-Micronized | 4 | 3.5 | 6.24 | 1.08 | 2.99 | 11.31 |
| Inhalac 250-Micronized | 4.5 | 4 | 3.91 | 0.96 | 2.56 | 6.66 |
| Inhalac 250-Micronized | 5 | 4 | 3.15 | 1.19 | 2.78 | 5.55 |
| Inhalac 250-Micronized | 5 | 4.5 | 3.51 | 1.06 | 2.64 | 6.05 |
| Inhalac 400 | N/A | N/A | 10.54 | 1.00 | 7.26 | 24.93 |
| Inhalac 400-Micronized | 4 | 3.5 | 2.56 | 0.75 | 1.92 | 4.43 |
| Inhalac 400-Micronized | 4.5 | 4 | 2.01 | 0.73 | 2.66 | 3.60 |
| Inhalac 400-Micronized | 5 | 4 | 2.64 | 0.76 | 1.93 | 4.28 |
| Inhalac 400-Micronized | 5 | 4.5 | 2.50 | 0.77 | 2.04 | 4.69 |

Formulation Preparation: Crystalline Compound 1 (Form B) was ground manually before mixing with lactose monohydrate (Inhalac 400) at the ratio of 1:4. The mixture was blended by manual grinding for 10 min. Then, the mixture was jet milled under the following conditions: injector gas pressure 4.5 bar, grinding gas 4 bar. PSD of dry dispersion data demonstrated the particle size of the formulation to be VMD=1.52 μm, $D_{10}$=0.63 μm, $D_{50}$=1.26 μm and $D_{90}$=2.77 μm.

In vivo mouse PK study: To demonstrate a delivery of Compound 1 to lung via inhalation route, a mouse (BALB/C) pharmacokinetic study was carried out. Mice were treated with a single dose of ~1 mg of the dry powder using an insufflator prior to sample collections. Plasma and lung samples were collected at different time points, and the drug concentrations in the mouse lung and plasma were determined. As shown in the table below, a rapid accumulation of high concentration of the drug in the lung tissue via inhalation route was observed. In contrast, the drug concentrations in plasma were significantly lower than those detected in the lung. These data show that delivery of Compound 1 can be effectively carried out via inhalation administration using the formulation disclosed, allowing Compound 1 to be in contact with, e.g., an influenza-infected respiratory tract. Interestingly, the drug level remained at least 100-fold excess of the therapeutic dose (anti-influenza potency, $EC_{50}$ 0.1-3 nM) on the fourth day. These results further confirmed a potential clinical use of Compound 1 dry powder for the treatment of influenza infection.

| Time point, hour | Drug concentration lung, μM | Drug concentration plasma, μM |
|---|---|---|
| 1 | 984 | 5.6 |
| 24 | 218 | 0.081 |
| 48 | 8.6 | 0.052 |
| 72 | 0.63 | 0 |
| 96 | 0.35 | 0 |

What is claimed:

1. A formulation comprising:
(a) crystalline 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (Compound 1) having an x-ray powder diffraction (XRPD) pattern exhibiting 2θ values of 5.6, 6.8, 8.4, 10.1, 10.6, 11.3, 15.1, 15.8, 18.0, 18.5, 19.1, 20.4, and 20.9, +0.2° (designated "Form B"), wherein the crystalline Compound 1 is present as a micronized crystal form; and
(b) a filler,
wherein the formulation is adapted as an inhalable formulation.

2. The formulation of claim 1, wherein the formulation is a powder formulation for inhalation administration, wherein the filler consists essentially of lactose monohydrate, and the formulation has a particle size distribution characterized by a volume mean diameter (VMD) of 1 to 2 μm, with a $D_{10}$ of 0.5 μm to 0.7 μm, a $D_{50}$ of 1 μm to 1.4 μm, and a $D_{90}$ of 2.5 μm to 2.8 μm.

3. The formulation of claim 1, wherein the filler comprises lactose.

4. The formulation of claim 1, wherein the filler is micronized.

5. The formulation of claim 1, wherein the crystalline Compound 1 has a melting point of 280° C. to 283° C.

6. The formulation of claim 1, wherein the crystalline Compound 1 has a volume mean particle size diameter of 0.5 to 10 μm.

7. The formulation of claim 1, wherein the filler has a volume mean particle size diameter of 0.5 to 10 μm.

8. The formulation of claim 1, wherein the ratio of the crystalline Compound 1 to the filler is 1:3 to 1:5, as a weight ratio.

9. A method of treating or preventing influenza virus infection or replication in a subject in need thereof comprising administering to the subject the formulation of claim 1 in an amount effective to treat the influenza infection.

10. A method of preparing the formulation of claim 1 comprising:
(a) micronizing the crystalline Compound 1 to form particles of Compound 1;
(b) optionally micronizing the filler to form particles of the filler; and
(c) blending the particles of Compound 1 and the optionally micronized filler to form the formulation.

11. The method of claim 10, further comprising crystalizing Compound 1 to form crystalline Compound 1 Form B prior to the micronizing step.

12. The method of claim 11, wherein the crystalizing comprises admixing Compound 1 and ethanol at a temperature of at least 50° C., cooling to room temperature to allow for crystallization of Compound 1, and collecting the crystals via filtration, and optionally drying the crystals prior to micronizing.

13. The method of claim 12, wherein Compound 1 and ethanol are admixed at a temperature of 75° C.

14. A crystalline 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (Compound 1) designated Form B, having an x-ray powder diffraction (XRPD) pattern exhibiting 2θ values of 5.6, 6.8, 8.4, 10.1, 10.6, 11.3, 15.1, 15.8, 18.0, 18.5, 19.1, 20.4, and 20.9, ±0.2°.

15. The formulation of claim 6, wherein the crystalline Compound 1 has a volume mean particle size diameter of 1.5 μm to 5 μm.

16. The formulation of claim 7, wherein the filler has a volume mean particle size diameter of 1.5 μm to 5 μm.

17. The method of claim 10, wherein the micronizing of the crystalline Compound 1 or the filler is via jet milling or manual grinding.

18. The method of claim 13, wherein Compound 1 and ethanol are admixed at a temperature of 75° C. for 4 to 10 hours.

19. The crystalline Compound 1 of claim 14, having a melting point of 280° C. to 283° C.

* * * * *